US008833942B2

(12) United States Patent
Zhuo et al.

(10) Patent No.: US 8,833,942 B2
(45) Date of Patent: Sep. 16, 2014

(54) METHOD AND DEVICE FOR MONITORING RETINOPATHY

(75) Inventors: Lang Zhuo, Singapore (SG); Saravana Kumar, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 91 days.

(21) Appl. No.: 13/509,428

(22) PCT Filed: Nov. 12, 2009

(86) PCT No.: PCT/SG2009/000422
§ 371 (c)(1),
(2), (4) Date: May 11, 2012

(87) PCT Pub. No.: WO2011/059405
PCT Pub. Date: May 19, 2011

(65) Prior Publication Data
US 2012/0229770 A1    Sep. 13, 2012

(51) Int. Cl.
A61B 3/10 (2006.01)
A61B 3/02 (2006.01)
G01N 21/64 (2006.01)
A61B 3/12 (2006.01)

(52) U.S. Cl.
CPC ........... *G01N 21/6486* (2013.01); *A61B 3/1241* (2013.01); *A61B 3/1225* (2013.01)
USPC ........................................ 351/221; 351/243

(58) Field of Classification Search
USPC ......... 351/221, 200, 205, 212, 222, 243, 245, 351/246
See application file for complete search history.

(56) References Cited

U.S. PATENT DOCUMENTS

| 6,478,424 B1 | 11/2002 | Grinvald et al. |
| 6,501,003 B1 | 12/2002 | Messing et al. |
| 6,611,704 B1 * | 8/2003 | van Best et al. ............... 600/476 |
| 7,847,090 B2 * | 12/2010 | Reich et al. ................... 536/24.5 |

FOREIGN PATENT DOCUMENTS

| WO | WO-2005/079238 A2 | 9/2005 |
| WO | WO-2006/041625 A2 | 4/2006 |
| WO | WO-2011/059405 A1 | 5/2011 |

OTHER PUBLICATIONS

Corrected International Search Report and Written Opinion mailed Dec. 24, 2009 in connection with PCT/SG2009/00042.
Response to Written Opinion and Demand filed Oct. 12, 2010 in connection with PCT/SG2009/000422.
International Preliminary Report on Patentability mailed Nov. 10, 2010 in connection with PCT/SG2009/000422.
Aiello et al., Diabetic retinopathy. Diabetes Care, Jan. 1998, pp. 143-156, vol. 21, Issue 1.
Antonetti et al., Diabetic retinopathy: seeing beyond glucose-induced microvascular disease. Diabetes, Sep. 2006, pp. 2401-2411, vol. 55, Issue 9.

(Continued)

*Primary Examiner* — Joseph P Martinez
*Assistant Examiner* — Brandi Thomas
(74) *Attorney, Agent, or Firm* — Wolf, Greenfield & Sacks, P.C.

(57) ABSTRACT

There is provided a method of monitoring retinopathy in a subject. The method involves measuring autofluorescence of a retina of the subject in response to high intensity blue light over a total time period to obtain an autofluorescence intensity profile. The autofluorescence intensity profile is processed to assess the retinopathy status of the retina.

16 Claims, 6 Drawing Sheets

(56) References Cited

OTHER PUBLICATIONS

Barnard et al., Melanopsin Regulates Visual Processing in the Mouse Retina. Current Biology, Feb. 21, 2006, pp. 389-395, vol. 16, Issue 4.
Belenky et al., Melanopsin retinal ganglion cells receive bipolar and amacrine cell synapses. The Journal of Comparative Neurology, Jun. 2, 2003, pp. 380-393, vol. 460, Issue 3. Epub the week of Apr. 14, 2003.
Berson, Phototransduction in ganglion-cell photoreceptors. Pflugers Archiv—European Journal of Physiology, Aug. 2007, pp. 849-855, vol. 454, No. 5. Epub Mar. 10, 2007.
Bos, Clinical quantitative pupillometry: The latency of pupillary constriction as measured with the IRIS system (preliminary results). Neuro-Ophthalmology, (month not listed on publication) 1988, pp. 299-305, vol. 8, No. 6.
de Vos et al., The pupillary light reflex in diabetes mellitus: evaluation of a newly developed infrared light reflection method. Diabetes Research Clinical and Experimental, Apr. 1989, pp. 191-195, vol. 10, Issue 4.
Do et al., Photon capture and signaling by melanopsin retinal ganglion cells. Nature, Jan. 15, 2009, pp. 281-287, vol. 457, No. 7227. Epub Dec. 31, 2008.
Fountas et al., Clinical implications of quantitative infrared pupillometry in neurosurgical patients. Neurocritical Care, Aug. 2006, pp. 55-60, vol. 5, No. 1.
Fu et al., Intrinsically photosensitive retinal ganglion cells detect light with a vitamin A-based photopigment, melanopsin. Proceedings of the National Academy of Sciences of the United States of America, Jul. 19, 2005, pp. 10339-10344, vol. 102, Issue 29.
Gardner et al., Diabetic Retinopathy: More Than Meets the Eye. Survey of Ophthalmology, Dec. 2002, pp. S253-S262, vol. 47, Supplement 2.
Gastinger et al., Dendrite Remodeling and Other Abnormalities in the Retinal Ganglion Cells of Ins2Akita Diabetic Mice. Investigative Ophthalmology & Visual Science, Jun. 2008, pp. 2635-2642, vol. 49, Issue 6.
Grozdanic et al., Evaluation of Retinal Status Using Chromatic Pupil Light Reflex Activity in Healthy and Diseased Canine Eyes. Investigative Ophthalmology & Visual Science, Nov. 2007, pp. 5178-5183, vol. 48, Issue 11.
Guler et al., Melanopsin cells are the principal conduits for rod-cone input to non-image-forming vision. Nature, May 1, 2008, pp. 102-105, vol. 453, No. 7191. Epub Apr. 23, 2008.
Hankins et al., Melanopsin: an exciting photopigment. Trends in Neuroscience, Jan. 2008, pp. 27-36, vol. 31, Issue 1. Epub Dec. 4, 2007.
Hattar et al., Melanopsin and rod-cone photoreceptive systems account for all major accessory visual functions in mice. Nature, Jul. 3, 2003, pp. 76-81, vol. 424, No. 6944. Epub Jun. 15, 2003.
Hattar et al., Melanopsin-Containing Retinal Ganglion Cells: Architecture, Projections, and Intrinsic Photosensitivity. Science, Feb. 8, 2002, pp. 1065-1070, vol. 295, No. 5557.
Hreidarsson, Pupil size in insulin-dependent diabetes. Relationship to duration, metabolic control, and long-term manifestations. Diabetes, May 1982, pp. 442-448, vol. 31, Issue 5 Part 1.
Kuroda et al., Pupillary light reflex in borderline diabetes mellitus. Diabetes Research and Clinical Practice, Feb. 15, 1989, pp. 89-94, vol. 6, Issue 2.
Leung et al., In vivo imaging of murine retinal ganglion cells. Journal of Neuroscience Methods, Mar. 15, 2008, pp. 475-478, vol. 168, Issue 2. Epub Nov. 7, 2007.
Lieth et al., Retinal neurodegeneration: early pathology in diabetes. Clinical & Experimental Ophthalmology, Feb. 2000, pp. 3-8, vol. 28, Issue 1.
Lin et al., Restoration of visual function in retinal degeneration mice by ectopic expression of melanopsin. Proceedings of the National Academy of Sciences of the United States of America, Oct. 14, 2008, pp. 16009-16014, vol. 105, Issue 41.
Lorenzi et al., Early cellular and molecular changes induced by diabetes in the retina. Diabetologia, Jul. 2001, pp. 791-804, vol. 44, No. 7.
Lucas et al., Characterization of an ocular photopigment capable of driving papillary constriction in mice. Nature Neuroscience, Jun. 2001, pp. 621-626, vol. 4, Issue 6.
Lucas et al., Diminished Pupillary Light Reflex at High Irradiances in Melanopsin-Knockout Mice. Science, Jan. 10, 2003, pp. 245-247, vol. 299, No. 5604.
Maass et al., Assessment of Rat and Mouse RGC Apoptosis Imaging in Vivo with Different Scanning Laser Ophthalmoscopes. Current Eye Research, (month not listed on publication) 2007, pp. 851-861, vol. 32, No. 10.
Martin et al., Death of Retinal Neurons in Streptozotocin-Induced Diabetic Mice. Investigative Ophthalmology & Visual Science, Sep. 2004, pp. 3330-3336, vol. 45, Issue 9.
Same, Landmarks in the historical development of fluorescein angiography. Journal of Ophthalmic Photography, Apr. 1993, pp. 17-23, vol. 15, No. 1.
Schmidt et al., Functional and Morphological Differences among Intrinsically Photosensitive Retinal Ganglion Cells. The Journal of Neuroscience, Jan. 14, 2009, pp. 476-482, vol. 29, Issue 2.
Scholl, Dendritic organization in the neurons of the visual and motor cortices of the cat. Journal of Anatomy, (month not listed on publication) 1953, pp. 387-406, vol. 87, Part 4.
Schwartz et al., Pharmacotherapies for Diabetic Retinopathy: Present and Future. Experimental Diabetes Research, (month not listed on publication) 2007, vol. 2007, Article ID 52487 (8 pages).
Sekaran et al., Melanopsin-Dependent Photoreception Provides Earliest Light Detection in the Mammalian Retina. Current Biology, Jun. 21, 2005, pp. 1099-1107, vol. 15, Issue 12. Epub May 26, 2005.
Serrarbassa et al., New concepts on diabetic retinopathy: neural versus vascular damage. Arquivos Brasileiros de Oftalmologia, May-Jun. 2008, pp. 459-463, vol. 71, No. 3. English Abstract provided (at the end of the publication).
Smith, The Impact of Diabetes on Neuronal, Glial, and Vascular Cells of the Retina: Implications for the Pathogenesis of Diabetic Retinopathy. Ophthalmology Research: Retinal Degenerations: Biology, Diagnostics, and Therapeutics, Edited by: J Tombran-Tink and C.J. Barnstable, Humana Press, (month not listed on publication) 2007, pp. 165-183.
Tu et al., Physiologic Diversity and Development of Intrinsically Photosensitive Retinal Ganglion Cells. Neuron, Dec. 21, 2005, pp. 987-999, vol. 48, Issue 6.
Wang et al., Loss of melanopsin-containing retinal ganglion cells in a rat glaucoma model. Chinese Medical Journal, (month not listed on publication) 2008, pp. 1015-1019, vol. 121, Issue 11.
Wong et al., Photoreceptor Adaptation in Intrinsically Photosensitive Retinal Ganglion. Neuron, Dec. 21, 2005, pp. 1001-1010, vol. 48, Issue 6.

\* cited by examiner

METHOD AND DEVICE FOR MONITORING RETINOPATHY

RELATED APPLICATIONS

This application is a U.S. National Stage application under §371 based on International Application No. PCT/SG2009/000422, filed Nov. 12, 2009, the contents of which is incorporated herein by reference in its entirety.

FIELD OF THE INVENTION

The present invention relates to methods and devices for monitoring retinopathy, including retinal neuropathy and diabetic retinopathy.

BACKGROUND OF THE INVENTION

Retinopathy is a non-inflammatory degenerative disease of the retina that leads to visual field loss or blindness. Retinopathy can be caused by various ophthalmic conditions as well as numerous systemic diseases outside the eye, for example diabetes. Diabetic retinopathy is an eye disease that results from damage to the retina as a result of complications such as nerve damage arising from diabetes mellitus. Diabetic retinopathy affects more than 80% of all patients who have had diabetes for 10 years or more and is the leading cause of vision loss in developed countries (Aiello et al., 1998).

Many retinal disorders can be diagnosed with the aid of retinal examination. Fluorescein angiography (FA) is the current standard technique used in diagnosis of diabetic retinopathy (DR) and is useful in detecting late-stage clinical hallmarks of DR, including retinal neovascularization (Saine, 1993). Laser photocoagulation, which has been applied in DR treatment for over half a century (Antonetti et al., 2006), is also a late-stage based treatment. Laser photocoagulation is successful in arresting proliferative diabetic retinopathy (PDR) in only 50% of cases. Even where further degeneration is prevented, any vision loss already incurred cannot be restored (Schwartz and Flynn, 2007).

Neuronal cell death in the retina (i.e. neuropathy) has been implicated in the early stages of DR, occurring much earlier than vascular damage becomes evident via FA techniques (Antonetti et al., 2006; Leith et al., 2000; Lorenzi et al, 2001; Gardner et al., 2002; Smith, 2007; Serrarbassa et al., 2008). Diabetic neuropathy affects the entire spectrum of retinal neurons, including the ganglion, horizontal, amacrine and photoreceptor cells (Antonetti et al., 2006; Smith, 2007). In fact, a reduction in the thickness of the neuronal cell layers in the retina due to diabetes has been reported in both experimental mice and human patients (Leith et al., 2000).

Pupillary light reflex (PLR) refers to the dilation/constriction of the pupil in response to light reaching the retina. High intensity light on the retina results in constriction in order to reduce the total light reaching the retina, and conversely, low intensity light results in pupil dilation in order to increase the light entering the eye and reaching the pupil. PLR can provide a useful diagnostic tool, allowing for testing of the sensory and motor responses of the eye. Lesions or disruptions in the eye can be detected by testing the direct response of a particular eye exposed to light entering the pupil as well as the consensual response of the eye when the opposite eye is exposed to light entering the pupil.

PLR has conventionally been used in the clinical setting to characterize the early effects of diabetic neuropathy (Hreidarsson, 1982; Devos et al., 1989; Kuroda et al., 1989). Such methods involve direct measurement of the pupil diameter or area in response to intense light. A pupillometer light source is generally focused on the pupil area, since the emphasis is on obtaining a bright and contrasting pupil image so that the pupil area can be accurately measured. This is an important consideration particularly in cases where poor pupil-iris contrast is obtained.

However, the early effects of retinopathy, which include diabetic neuropathy, on PLR can only be objectively assessed if light is directed onto the site of possible disease, that is, the photoreceptive retinal neurons. Thus, in order to use PLR as an indicator of early retinopathy, not only must the intensity level of the light source be controlled, but also the amount of light that reaches the retina must also be controlled (Fountas et al., 2006), which can be complicated, since slight changes in lens opacity and matrix of the eye may affect the amount of light actually reaching the retina. The initial pupil size may also affect the amount of light incident on the retina and influence the resultant pupillary constriction. As well, monitoring PLR by direct measurement of pupil size, such as pupil area or diameter, does not take into account the amount of stimulus light incident on the retina. Determining and standardizing the amount of light incident on the retina during diagnosis can present difficulties, particularly in longitudinal and quantitative studies of retinopathy.

Effective early detection and preventive treatment of retinopathy, including diabetic retinopathy would help to minimize complications such as permanent vision loss due to late-stage treatment provided by laser photocoagulation.

SUMMARY OF THE INVENTION

The present invention relates to methods of monitoring retinopathy in a subject. Irradiation of the retinal ganglion cell (RGC) layer containing melanopsin-expressing retinal ganglion cells (mRGCs) with high intensity blue light results in constriction of the pupil. Measurement of PLR is typically used to assess early stages of retinopathy. The methods of the present invention use the autofluorescence (AF) of the RGC layer as an indicator of the level of PLR to monitor the retinopathy status of the retina.

The methods of the present invention are based on measuring the AF of the RGC layer containing mRGCs in response to high intensity blue light. An intensity profile of AF over time is obtained for a retina of a subject. The obtained profile is then processed in order to assess the retinopathy status of the retina.

In one aspect, the present invention provides a method of monitoring retinopathy in a subject, the method comprising: directing high intensity blue light at the retina of an eye of the subject; measuring autofluorescence of the retina in response to the blue light over a total time period to obtain an autofluorescence intensity profile; and processing the autofluorescence intensity profile to assess the retinopathy status of the retina.

The blue light may have a wavelength of from about 485 nm to about 490 nm, and in particular a wavelength of about 488 nm.

A confocal light source and/or a laser light source may be used to produce the blue light. In particular, a confocal scanning laser ophthalmoscope may be used in the methods of the invention.

The processing may include integrating area under the curve for the autofluorescence intensity profile.

The assessing may include comparing the processed autofluorescence intensity profile with a processed autofluorescence intensity profile obtained for retina of a non-diseased individual. Alternatively, the assessing may include comparing the processed autofluorescence intensity profile with a processed autofluorescence intensity profile obtained for the same retina of the subject.

In another aspect, the present method provides a diagnostic tool for monitoring retinopathy, the diagnostic tool comprising: a light source for generating high intensity blue light; a detector for detecting autofluorescence of a retina in response to the blue light; a memory, the memory storing instructions; and a processor in communication with the light source, the detector and the memory. The processor executes instructions to: activate the light source to generate the high intensity blue light directed at the retina of an eye of a subject; obtain an autofluorescence profile over a total time period from measurements at the detector; and process the autofluorescence intensity profile to assess the retinopathy status of the retina.

The diagnostic tool may be as described above for performing the method of the present invention.

In another aspect, the present invention provides a computer-readable medium storing executable instructions that, upon execution by a processor of a computing device, causes the computing device to facilitate monitoring of retinopathy by: generating high intensity blue light for directing at the retina of an eye of a subject; measuring autofluorescence of the retina in response to the blue light over a total time period to obtain an autofluorescence profile; and processing the autofluorescence intensity profile to assess the retinopathy status of the retina.

In yet another aspect, the present invention provides use of an autofluorescence intensity profile obtained for a retina in response to high intensity blue light over a total time period, for monitoring retinopathy in a subject.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

The presently described method relates to indirect measurement of PLR by measuring retinal AF from a retina over a time course, due to stimulation of mRGCs with high intensity blue light.

The method measures the mRGC-mediated PLR response, since mRGCs are known to be intrinsically photosensitive (Lucas et al., 2001; Hattar et al., 2002; Tu et al., 2005; Wong et al., 2005; Schmidt and Kofuji, 2009). The mRGCs belong to a family of photosensitive neurons in the RGC layer that transduce light into electrical impulses which are then transmitted to the brain and processed. An appropriate response is then sent from the brain to the iris to regulate the size of the pupil.

The mRGCs play a complementary role with rod-cone photoreceptors in mediating PLR (Lucas et al., 2001; Hattar Et al., 2002; Tu et al., 2005; Belenky et al., 2003; Hattar et al., 2003; Lucas et al., 2003; Fu et al., 2005; Sekaran et al., 2005; Barnard et al., 2006; Guler et al., 2008; Hankins et al., 2008). The rod-cone system is active over a broad range of light intensities with peak sensitivity at 520 nm. In contrast, the mRGC-mediated pathway activates pupillary constriction at high light intensity levels (Lucas et al., 2003) and is most sensitive to blue light excitation, particularly at 488 nm (Lucas et al., 2001; Lucas et al., 2003; Grozdanic et al., 2007).

The AF obtained in response to the blue light is from AF aggregates within the RGC layer, for example lipofuscin pigments as well as advanced glycation end products, among others.

The method is based on obtaining an AF intensity profile of a retina over time. An AF intensity profile refers to the autofluorescence intensity measured in response to stimulation of the retina with the high intensity blue light over a given period of time, for example by taking successive time point measurements of AF intensity within a total time period, as described below.

The AF intensity profile obtained is processed and used to assess the retinopathy status of the retina. The AF intensity can be used as an indicator of the pupil size since the pupil regulates the amount of blue light that reaches the retina, which in turn regulates the AF that is emitted. The AF intensity profile obtained over time can be used as an indicator of the PLR, which in turn is an indicator of the health of retinal neurons. Thus, the AF intensity profile can be used to identify or monitor retinopathy.

This indirect measurement approach is a label-free imaging method that provides indirect assessment of the PLR of a retina, and may be used to monitor retinopathy, including retinal neuropathy and early stages of diabetic retinopathy, given the neuronal cell death associated with retinal neuropathy, including death of the mRGCs.

Thus, there is provided a method of monitoring retinopathy. The method comprises directing high intensity blue light at a retina in an eye of a subject in order to autofluoresce the retina; measuring the AF of the retina in response to the blue light over a total time period to obtain an AF intensity profile; processing the AF intensity profile in order to assess the retinopathy status of the retina.

In practising the method, high intensity blue light is directed at the retina of a subject in whom retinopathy is to be monitored, and in particular at the RGC layer, containing the mRGCs.

Blue light has a wavelength in the range of from about 450 to about 495 nm. Blue light is used in the method, as the mRGCs are most sensitive to blue light, particularly to light of wavelength 488 nm. In certain embodiments, the wavelength of the blue light is in the range of about 485 nm to about 490 nm. In a particular embodiment, the blue light has a wavelength of about 488 nm. In one embodiment, the blue light has a wavelength of 488 nm.

High intensity light is intended to refer to light that is of sufficient intensity to enable the collection of AF signal from the retina of the subject. Whether light is of sufficient intensity can be readily determined, for example by testing the intensity of light on a subject. If the light does not induce AF of the retina, despite being of an appropriate wavelength, then the light is not considered to be high intensity. It will be appreciated that the intensity of the light, while of high enough intensity to allow for measurement of the AF signal for the retina, will not be of such high intensity so as to damage the retina of the subject. For example, the intensity of the blue light may be chosen in keeping with standard limits, for example those established by the American National Standards Institute (ANSI Z136.1, 1993), or in keeping with international standards for safe use within a clinical setting.

The blue light may have an intensity of about 1 mW/cm$^2$ or greater, about 2 mW/cm$^2$ or greater, about 5 mW/cm$^2$ or greater, about 10 mW/cm$^2$ or greater, from about 1 mW/cm$^2$ to about 100 mW/cm$^2$, from about 1.0 mW/cm$^2$ to about 10 mW/cm$^2$, about 2 mW/cm$^2$, about 5 mW/cm$^2$ or about 10 mW/cm$^2$. For this range and all ranges given throughout this specification, any narrower range falling within a stated range is also intended.

The high intensity blue light is used to induce AF of the RGC layer in an eye of the subject. The retina is composed of several layers of neurons, including the RGC layer where the mRGCs are located. Thus, the blue light is directed on the retina of the subject, including the RGC layer, including the mRGCs in the retina.

The high intensity blue light may be generated at the appropriate wavelength, for example, using a scanning laser device, such as a confocal scanning laser ophthalmoscope. Use of the confocal scanning laser ophthalmoscope as the light source also allows for use as a photodetector for measuring the intensity of AF measured by the mRGCs.

A confocal or focused light source may be used, as light from such a source allows the light to be focused directly at the RGC layer within the retina. Use of a confocal light source, for example using confocal scanning laser technology, enables the light to be accurately directed, via optical sectioning, at the RGC layer where the mRGCs are located. It also enables continuous exposure of the RGC layer to high intensity blue light, including for times as long as half an hour, without causing any harm to the subject.

In order to ensure the blue light is directed at the RGC layer so that AF will be induced, the RGC layer may be located within the retina by first reflecting infra-red (IR) light to saturate the optic disc with the IR reflected brightness. For example, using a confocal scanning laser ophthalmoscope, the ophthalmoscope may be first operated in IR reflectance mode (for example, excitation: 820 nm, emission: all pass) such that the reflected IR brightness is saturated all around the optic disc (i.e. the corresponding pixels on the detector exhibit maximum intensity values). This provides a confirmation that the light is indeed focused onto the RGC layer. The ophthalmoscope may then be switched back to the fluorescence mode so that the blue laser light replaces the IR light. This approach enables the operator to control the intensity of blue laser light irradiating the RGC layer by first controlling the brightness of the reflected IR light prior to operating the ophthalmoscope in the fluorescence mode.

If other factors are present which affect the passage of light to the retina, such as changes to the lens opacity and matrix of the eye as well as initial pupil size, the method allows for tuning of the intensity of the blue laser light source to ensure that a given intensity of blue laser light actually reaches and irradiates the RGC layer. This may be done by first tuning the IR light source so that the reflected IR brightness is comparable to a reference IR brightness value. A calibration curve can then be used to determine the corresponding change required in the intensity of the blue laser light source so that the given intensity of blue laser light irradiates the RGC layer.

If desired, the subject's pupils may be chemically dilated prior to directing the high intensity blue light at the retina, in order to increase the amount of light that reaches the retina. Pupil dilation using chemical dilators such as mydriatics is known. Mydriatics are commercially available, for example cyclopentolate hydrochloride and tropicamide, including in formulations for administration as a drop to the eye.

In order to perform the method, the blue light is directed to the retina, including the RGC layer, for a total period of time over which the AF is to be measured and over which an intensity profile is to be generated. Thus, during the entire measurement period, the retina is exposed to the high intensity blue light.

The AF generated by the RGC layer in response to the high intensity blue light is measured over the total time period, using known methods for detecting fluorescence signals. A detector, such as a photo-detector, is used to detect the fluorescence signal generated by the retina. For example, laser confocal microscopy methods may be used, as described in U.S. Pat. No. 6,501,003, which may employ scanning laser ophthalmoscopy techniques. Such techniques may involve a scanning laser ophthalmoscope using a laser beam from a point source and then detecting reflected light using a photomultiplier. A confocal scanning laser ophthalmoscope provides AF images of high resolution, allowing for more precise quantification of the AF intensity and thus providing a more accurate AF intensity over time profile.

For example, fluorescent images detected using fluorescent microscopy techniques including ophthalmoscopy methods may be captured by computer and quantified using standard imaging software. Fluorescence images, including digital images, may be recorded using a photo-detector. The intensity of the AF recorded in a digital image may be determined by calculating pixel intensity within the image. For example, the average pixel intensity within a pre-determined area of an image may be calculated and used as the AF intensity for that image.

The light is directed to the retina and AF is measured over a total period of time. The total time period is a time period sufficient to measure the AF of the RGC layer and obtain an intensity versus time profile. The total time period may be, for example, 1 minute, 2 minutes, 5 minutes, or any time period falling within the range of from 30 seconds to 10 minutes. Sequential measurements of two or more AF measurements may be taken at time intervals over the total time period in order to generate a time course of measurements and obtain a profile of AF intensity over time. Measurements may be taken at any suitable time interval, for example: every 2 seconds, every 3 seconds, every 5 seconds, every 10 seconds or at any time interval falling within the range of from 2 to 20 seconds.

The AF measurements obtained may optionally be normalized with respect to an initial measurement (e.g. time=0) in order to produce relative AF values, which are thus expressed as a fraction, or relative amount of the initial AF measurement.

As indicated above, a series of intensity measurements are taken at time points throughout the total time period, resulting in a profile of AF intensity over time. If desired, the AF intensity profile may be expressed as a curve of intensity versus time, or relative intensity versus time.

The AF intensity profile is then processed in order to assess the retinopathy status of the retina for which the profile is obtained.

Processing includes any data manipulation or transformation applied to the data contained within the AF intensity profile. Processing may be performed on part or all of the profile. Processing may, for example, involve integration to obtain an area under the curve, taking a derivative of a portion or all of the profile, statistical analysis of the profile, averaging of the profile, application of filters, or image processing, for example to analyse morphological data contained within the digital images obtained during measurement.

In one embodiment, processing comprises integration of the AF intensity profile. The time course of AF measurements or relative AF is integrated over the total time period. An area under the curve is thus computed.

In addition to manipulation of the AF intensity profile, processing further includes using the processed intensity profile to assess the retinopathy state of the retina for which the intensity profile was obtained; that is, the processed intensity profile may be used to monitor the state of the neurons within the retina and the ability of the RGC layer to autofluoresce in response to high intensity blue light, and thus detect and/or monitor retinopathy within the eye. The processed intensity profile is thus used as an indirect assessment of the PLR of the particular retina tested, without any need to directly assess pupil diameter or area, allowing for assessment of the health of the retina and possible detection or monitoring even of early stages of retinopathy.

Retinopathy refers to any disease, disorder or condition which may cause, result in, or is associated with retinal degeneration including degeneration of the photoreceptors or mRGC neurons. The retinopathy may be any retinopathy, including primary retinopathy or secondary retinopathy, and includes, for example, degeneration of retinal neurons, neuropathy, glaucoma, retinitis pigmentosa and diabetic retinopathy. Retinopathy includes retinal gliosis, retinal degeneration or retinopathy related to neurodegenerative diseases including Parkinson's disease and Alzheimer's disease, primary retinopathies originating from the eye including retinoschisis, age-related macular degeneration and glaucoma, and secondary retinopathies originated from systemic diseases including diabetic retinopathy, hepatic retinopathy, renal retinopathy, hypertension, vascular diseases, congenital heart disease, autoimmune disorders including rheumatoid arthritis, multiple sclerosis, neurofibromatosis, Lyme neuroborreliosis, Down's syndrome, autism, sickle cell anaemia, infections with HIV and cytomegalovirus, thyroid disorders, or liver disorders.

The retinopathy status of a retina refers to the presence or absence of retinopathy or the extent of retinopathy or retinal degeneration in a particular subject at a particular point in time. Retinopathy status includes the stage of disease, including the stage prior to onset, as well as the extent of disease.

Retinopathy status may be assessed by comparing a processed AF intensity profile obtained for the retina of interest with a reference value. The reference value may be a value obtained from a processed AF intensity profile for an individual with a known retinopathy status, for example an individual known to have healthy, non-diseased retinas, or may be obtained for the same subject at an earlier point in time.

Thus, processing may include comparing the processed AF intensity profile for a particular retina with reference values obtained for an individual with a healthy, non-disease retina, in order to diagnose retinopathy or to monitor retinopathy progression within the eye of the subject. Thus, an individual that does not have retinopathy, or who is not at significant risk of developing retinopathy, or who does not have a known pre-disposition for developing retinopathy may be used to provide a standard of processed AF intensity profile in a healthy, non-disease retina, which standard is not indicative of or related to retinopathy, thus allowing for comparison of disease status in a subject that has, is suspected to have or that may be pre-disposed to develop retinopathy and an individual being free from any such pathology or pre-disposition. The value obtained for a particular retina may be compared with a reference value, in order to determine the retinopathy status of the retina and thus the eye. In this way, the processed intensity profile for the subject in the method may be used to diagnose the presence, onset or extent of retinopathy, including at stages earlier than typically possible using direct measurement of PLR.

Alternatively, processing may include comparing the processed AF intensity profile obtained in the method with a reference processed AF intensity profile value obtained at an earlier point in time for the same retina in the same subject, as a method of monitoring disease onset, disease progression, or disease regression in the subject. For example, comparison may be made between a current value and a value obtained from 1 to 4 weeks, from 1 to 9 months or from 1 to 5 years earlier for the same retina of the subject on which the method is currently performed.

It will be appreciated that in order to perform a relevant comparison, the method parameters used to obtain the reference value should be comparable to those used in the method for monitoring retinopathy. For example, using the same intensity and wavelength of blue light source and the same intensity of blue light irradiating the RGC layer, and comparing areas for the same total time period, and performing the same processing technique allows for comparison between retinas. As stated above, if factors such as the lens opacity, matrix of the eye and the initial pupil size for a given eye of a subject are such that the actual intensity of light irradiating the RGC layer is affected despite using a constant intensity of blue light from the light source, the intensity of the blue laser light source can be tuned so that the intensity of the blue light irradiating the RGC layer remains comparable with that used to obtain the reference value.

The subject on whom the method is performed is any subject for whom retinopathy is desired to be monitored. The subject may be any animal, including a mammal, including a human.

Monitoring retinopathy includes tracking disease onset, progression, regression, recovery or prognosis over a period of time and also includes tracking of response to treatment and tracking of side effects, including toxicity, of treatment, over a period of time. Thus, the monitoring may be performed during a treatment regimen for retinopathy by performing the method at various times throughout a time course of treatment or before, during or after treatment. Treatment may include dietary regimen, controlled environmental conditions, or administration of a therapeutic agent.

An assessment of the retina is a useful tool for determining the extent of an underlying disease in a non-invasive manner and may aid determination of prognosis and monitoring of disease progression in a patient. Due to its accessibility, examination of the retina may facilitate the assessment of therapeutic strategies and medical trials. Thus, the method described herein provides a non-invasive, label-free approach to quantitatively assess PLR of a retina in a subject.

The method is sensitive, since it relies on the AF from the RGC layer rather than measurement of the pupil itself, and therefore may allow for early detection of retinopathy, including retinal neuropathy and diabetic retinopathy, at a stage at which it may be possible to slow, prevent or reverse vision loss.

The method is more quantitative than the direct measurement of PLR since it can ensure a fixed amount of light reaches the RGC layer initially, allowing for a more reliable comparison between the processed AF intensity profiles of different subjects or at different time points in the same subject.

Also provided are uses of high intensity blue light to measure PLR of an eye of a subject, including use of an AF intensity profile obtained for a retina in response to high intensity blue light over a total time period, for monitoring retinopathy in a subject.

The above-described methods and uses may be facilitated by a diagnostic tool comprising a computing device.

Figure 1:
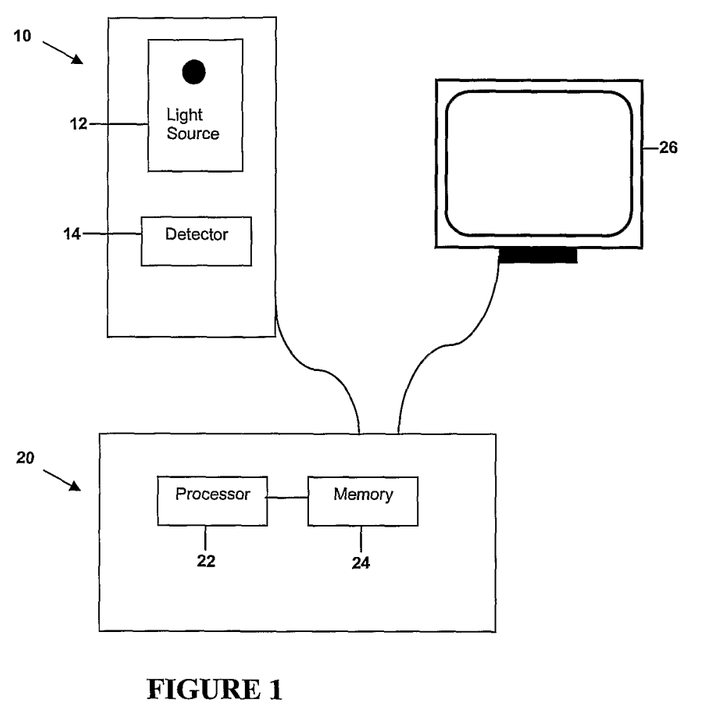
FIG. 1 is a schematic representation of a diagnostic tool comprising a computing device that can facilitate performance of methods of the present invention.

Referring to FIG. 1, the illustrated diagnostic tool 10 comprises a light source 12 for providing the high intensity blue light and a detector 14 for detecting AF from the retina in response to the blue light.

Light source 12 produces the high intensity blue light for the method as described above, including light having a wavelength in the range of about 485 nm to about 490 nm, or a wavelength of about 488 nm or a wavelength of 488 nm. Light source 12 may be, for example, a laser light source, a confocal light source, including a confocal laser. In a particular embodiment, light source 12 is a confocal scanning laser.

In one embodiment, diagnostic tool 10 comprises a confocal scanning laser ophthalmoscope, which includes a confocal scanning laser and a detector.

The diagnostic tool 10 further comprises, or is in communication with, a computing device 20 comprising a processor 22 and memory 24 in communication with the processor.

Processor 22 is typically a conventional central processing unit, and may for example be a microprocessor in the INTEL x86 family. Of course, processor 22 could be any other suitable processor known to those skilled in the art.

Memory 24 includes a suitable combination of random access memory, read-only-memory, and disk storage memory used by computing device 20 to store and execute software programs adapting diagnostic tool 10 to facilitate performance of the method.

Thus, computing device 20, including processor 22, is adapted to perform the method as described herein. For example, computing device 20 may control the wavelength and intensity of light generated by light source 12, and may communicate with detector 14 to receive and/or record the AF data detected by detector 14. Computing device 20, and in particular processor 22, may be involved in executing the processing of the AF data to produce a processed AF intensity profile, for example by transforming or manipulating data received from detector 14. Computing device 20 may also be involved in assessing the retinopathy status of a retina, for example by performing a comparison of a processed AF intensity profile with a reference value, such as a processed AF intensity profile obtained for a healthy, non-disease retina, or an earlier processed AF intensity profile, obtained at an earlier time point for a retina of the subject on which the method is performed.

The operation of the computing device and, in turn, the diagnostic tool, may be governed by software. The software, which takes the form of processor-executable instructions, may be loaded into the memory of the computing device from a machine-readable (e.g. computer-readable) medium, such as an optical disk or a magnetic storage medium for example.

The diagnostic tool may also further comprise, or may be in communication with, a display unit 26 for displaying the results of the method, for example, for displaying the measured AF, for displaying the obtained AF intensity profile, for displaying the processed AF intensity profile, or for displaying the results of assessing the retinopathy status of the retina. For example, the display unit 26 may be in communication with the computing device 20, which in turn is in communication with the diagnostic tool 10 comprising the light source 12 and detector 14.

As well, computing device 20 may optionally include input/output devices, such as a keyboard, disk drive and a mouse (all not shown) or the like.

Thus, the diagnostic tool may be a confocal scanning laser ophthalmoscope incorporating or in communication with the computing device.

The present methods and uses are further exemplified by way of the following non-limited examples.

EXAMPLES

The present study was designed to develop a novel method for quantifying PLR based on AF intensity (AFI) emitted due to confocal retinal blue light excitation (cRBLE) and to study longitudinal PLR alteration in a type 1 diabetic mouse model. Diabetes was triggered via a single intraperitoneal injection of streptozotocin (STZ) into wild type C57BL/6J mice. Anaesthethized mice were subjected to cRBLE weekly over a period of four weeks. At each time point, PLR was quantified by introducing the concept of the 'area under the curve' (AUC) of the intensity profile of retinal AF measured at 5 second (s) intervals over a period of 275 s. The mice develop diabetes as early as three days after STZ induction. The blood glucose levels peaked at approximately 23 mmol/L and the body weight decreased by approximately 20% after one month post-treatment. A progressive decrease in diabetic AUC occurred during this period but control AUC remained relatively unchanged. PLR was initiated despite synaptic blocking of the iris circular muscles during mydriasis followed by anaesthesia.

Research Design and Methods

Animal husbandry. 10-week old male C57BL/6J mice were used for the present study. Animals were housed at the Biological Resource Center in a controlled environment (room temperature at 21° C. and a 12 h light/dark cycle) with free access to food and water in Biopolis, Singapore. The experimental protocol covering the current study was approved by the Institutional Animal Care and Use Committee (IACUC).

Induction of diabetes. Diabetes was induced using the streptozotocin (STZ) pharmacological model. A single dose of streptozotocin (STZ), dissolved in sodium citrate buffer (0.1M, pH4.5), was administered intra-peritoneally to the mice at 200 mg/kg body weight. The mice developed diabetes within three days after administration. In the STZ-treated group 4), a base-line cRBLE was performed prior to the STZ treatment, followed by STZ treatment the very next day. cRBLE was performed once weekly for a total of 4 weeks. Saline was used as a vehicle for the control group (n=5). Care and use of animals adhered to the institutional guidelines for humane treatment of animals.

Determination of blood glucose. Mice were bled via tail-end puncture and the blood glucose levels were measured with a glucometer (AccuCheck; Roche Diagnostics Asia Pacific Pte. Ltd., Singapore). Mice with fasting blood glucose levels higher than 13.9 mmol/L were considered diabetic.

Preparation of animals. Mice were anaesthetized by intra-peritoneal (i.p.) injections with 0.15 ml/10 g body weight of Avertin (1.5% 2,2,2-tribromoethanol; T48402) purchased from Sigma-Aldrich (St. Louis, Mo., USA), and the pupils dilated with a drop of 0.5% Cyclogyl® sterile ophthalmic solution (cyclopentolate hydrochloride, Alcon®, Puurs, Belgium). Custom-made PMMA hard contact lenses (from Cantor & Nissel, Northamptonshire, UK) were used to avoid dehydration of the cornea and minimized spherical aberration of the mouse eye which could compromise the cRBLE procedure. Careful eye examination ruled out the presence of any corneal or lens opacities. The pupils were dilated for 15 minutes before the cRBLE procedure.

Confocal retinal blue light excitation (cRBLE). A commercially available confocal scanning laser ophthalmoscope (cSLO), the Heidelberg Retina Angiograph 2, HRA 2 (Heidelberg Engineering, Dossenheim, Germany) (26; 27), was used for the cRBLE procedure on the mice. The 30° focal lens was replaced with a 55° wide angle objective lens in order to allow more light to enter the small mouse pupil. The 100% argon laser power provided maximum excitation intensity at the desired wavelength of 488 nm (and emission at >500 nm). The laser was consistently focused on the RGC layers since this is the focal section where the mRGCs are located. This focal section was located by first operating the cSLO in the infra-red (IR) reflectance mode (excitation: 820 nm, emission: all pass) and by ensuring that the resultant IR brightness was saturated all around the optic disc with the laser power and photo-detector sensitivity fixed at 50% and 65% respectively. The cSLO was then switched back to fluorescence mode before acquiring the images. Pupillary constriction was measured indirectly based on the amount of AF emitted from the focal section by a photo-detector fixed at 93% sensitivity. The AF detected decreases as the pupil constricts. A series of time-lapse AF images at 5 s intervals for a period of 275 s was acquired for each mouse eye. The OS (left) eye was first subjected to cRBLE, after which the mouse was adapted in the dark for 10 minutes before the procedure was repeated on the OD (right) eye.

Image-based PLR quantification. An intensity profile of AF for a period of 275 s was obtained by computing the average pixel intensity of the corresponding image at each 5 s interval. The area under the 'intensity vs. time' curve (AUC) is then computed and used here as a measure of PLR. The AUC for a particular mouse on any given day and eye is normalized with respect to its day 0 (base-line) AUC. The quantified AUC values for a specific time point and experimental group, i.e. saline or STZ treated, are expressed as $\overline{AUC}\pm SEM$, where $\overline{AUC}$ denotes the average AUC value across all mice at a specific time point and experimental group whereas SEM denotes the corresponding standard error of the mean. The results were statistically tested using the Student's two-tailed t-test assuming unequal sample variance.

Immunohistochemistry. On day 28 post-STZ treatment, mice were killed by $CO_2$ asphyxiation in a gas chamber. The eyes were immediately enucleated and placed overnight in 4% paraformaldehyde (PFA) in phosphate buffered saline (PBS). The anterior part (cornea, lens, and vitreous) of the eye was removed and the retina was carefully isolated free of the pigment epithelium. The retinas were fixed in fresh 4% PFA in PBS for 30 minutes and then washed three times in PBS for 5 minutes each. The free-floating retinas were first blocked with 3% bovine serum albumin (BSA) for 1 hour at room temperature and were then incubated with a primary melanopsin antibody (polyclonal rabbit anti-melanopsin; Affinity Bioreagents, Golden, Col.) at 1:200 dilution in PBS/0.3% Triton X-100/3% bovine serum albumin for 72 hours at 4° C. After three washes in PBS of 15 minutes each, the fluorescence-conjugated secondary antibody (Alexa Fluor 594 goat antibody to rabbit immunoglobulin G; Molecular Probes, Eugene, Oreg., USA) was applied to the sample as previously described, except that incubation was for 2 hours at 37° C. The retinas were washed again as described above, flat mounted onto glass slides and coverslips were applied using Vect Mount Permanent Mounting Medium. (Vector Laboratories, Burlingame, Calif., USA).

FIGURE LEGENDS

Figure 2:
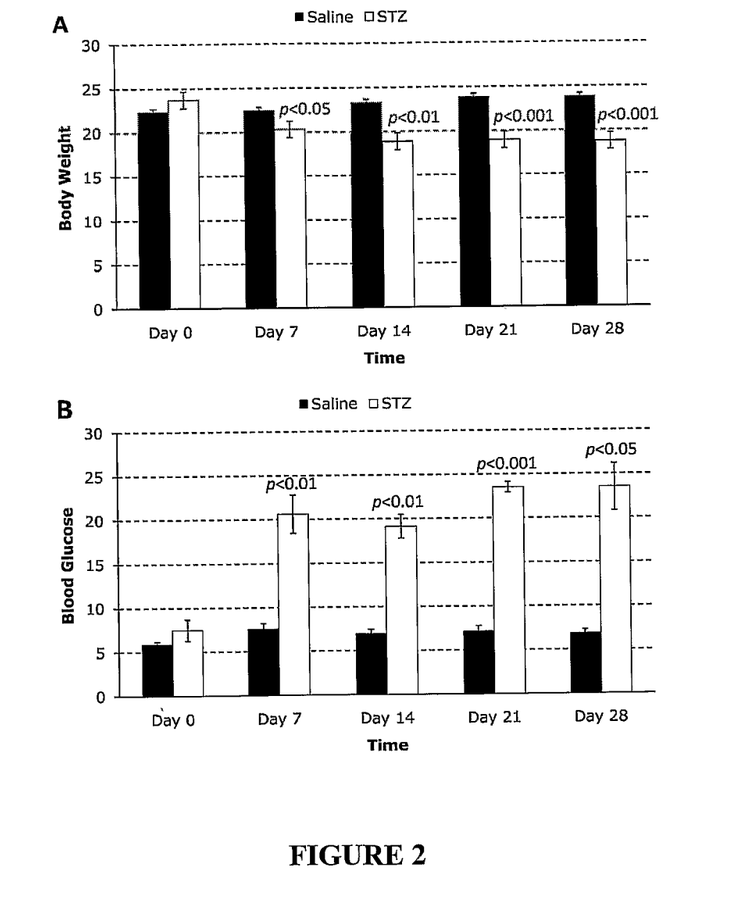
FIG. 2 graphically illustrates variation in weight (A) and blood glucose levels (B) between FVB/N mice treated with saline (■) or STZ (□)

FIG. 2. Longitudinal variation in average weights and blood glucose levels of saline (n=5) and STZ treated (n=4) FVB/N mice. The difference in mean body weight (A) between the two groups is significant on days 7 ($p<0.05$), 14 ($p<0.01$), 21 ($p<0.001$) and 28 ($p<0.001$). The difference in mean blood glucose levels (B) is also significant on days 7 ($p<0.01$), 14 ($p<0.01$), 21 ($p<0.001$) and 28 ($p<0.05$).

Figure 3:
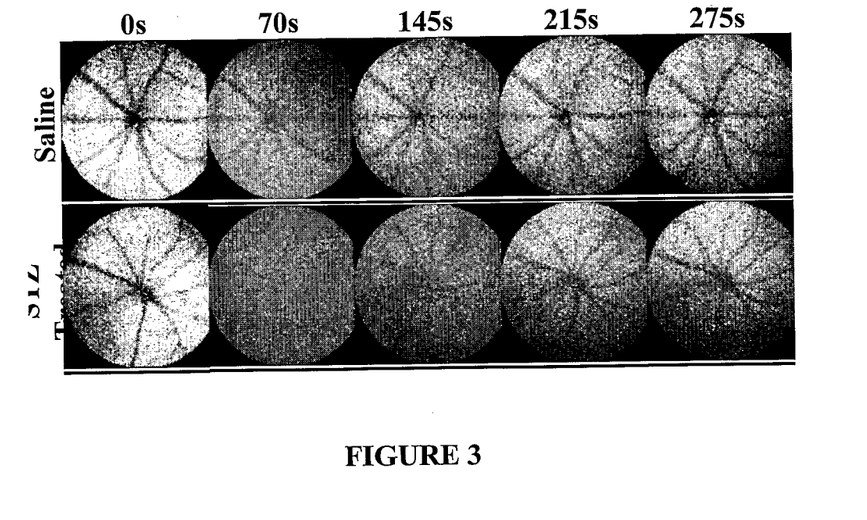
FIG. 3 is in vivo time-lapse AF images of retina of saline and STX treated C57BL/6J mice.

FIG. 3. In vivo time-lapse AF images of the saline and STZ treated wild type C57BL/6J mouse retina, centered around the optic disc, over a period of 275 seconds. The AFI is a measure of the mouse pupil size and both saline and STZ treated mice have comparable intensity levels at t=0 seconds. But subsequently the STZ treated mice show a more distinct fall in AFI compared to saline as shown at t=70 s. The STZ treated mice also show a slower recovery in AFI as shown from t=70-275 seconds. All images have been denoised and contrast-enhanced.

Figure 4:
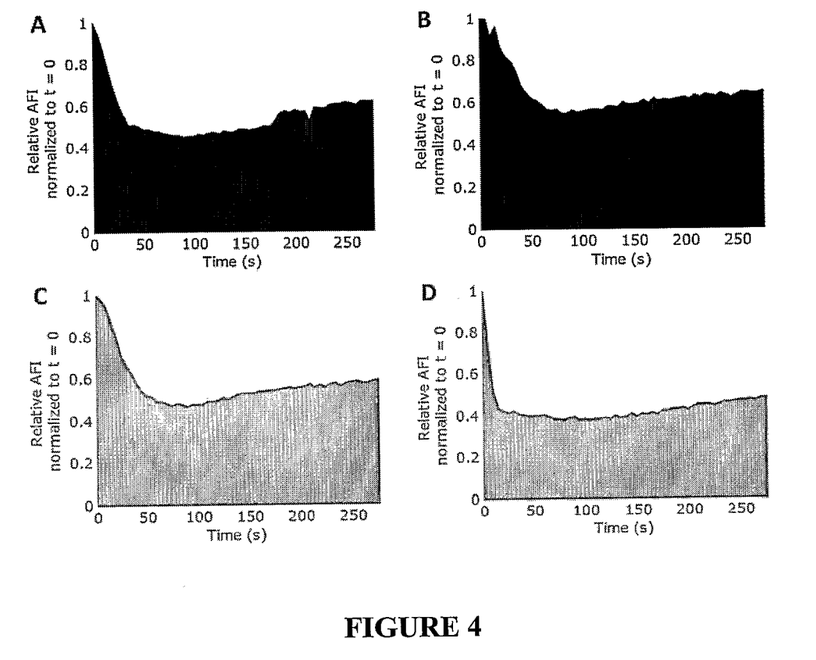
FIG. 4 is representative AF intensity profiles for saline (A, B) and STZ (C, D) mice taken on day 0 (A, C) and day 28 (B, D)

FIG. 4. Comparison of representative AFI profiles for saline on day 0 (A) and day 28 (B) and STZ treated mice on day 0 (C) and day 28 (D). Each AFI profile has a series of AFI values at 5 second intervals over a period of 275 seconds. Each AFI value has been normalized with respect to its t=0 value. The AUC for the saline and STZ treated mice are labelled blue (A, B) and red (C, D) respectively.

Figure 5:
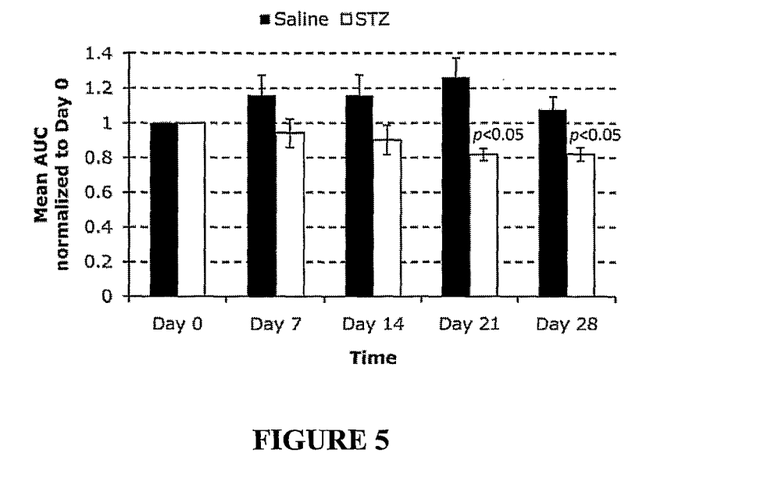
FIG. 5 graphically illustrates variation in the mean area under the curve of saline (■) and STZ (□) treated groups.

FIG. 5. Longitudinal variation in the mean AUC ($\overline{AUC}$) of the saline (n=5) and the STZ treated (n=4) groups. The AUC measurements for day 0 were normalized to 1, as a reference for comparing the later longitudinal time points. The $\overline{AUC}$ value of the STZ treated group drops steadily from days 0-28. But the saline group shows a higher $\overline{AUC}$ from days 7-28 relative to its base-line value. The difference between the two groups is significant on days 21 ($p<0.05$) and 28 ($p<0.05$). The mean AUC values were expressed as $\overline{AUC}\pm SEM$ and statistically tested using the Student's two-tailed t-test assuming unequal sample variance.

Figure 6:
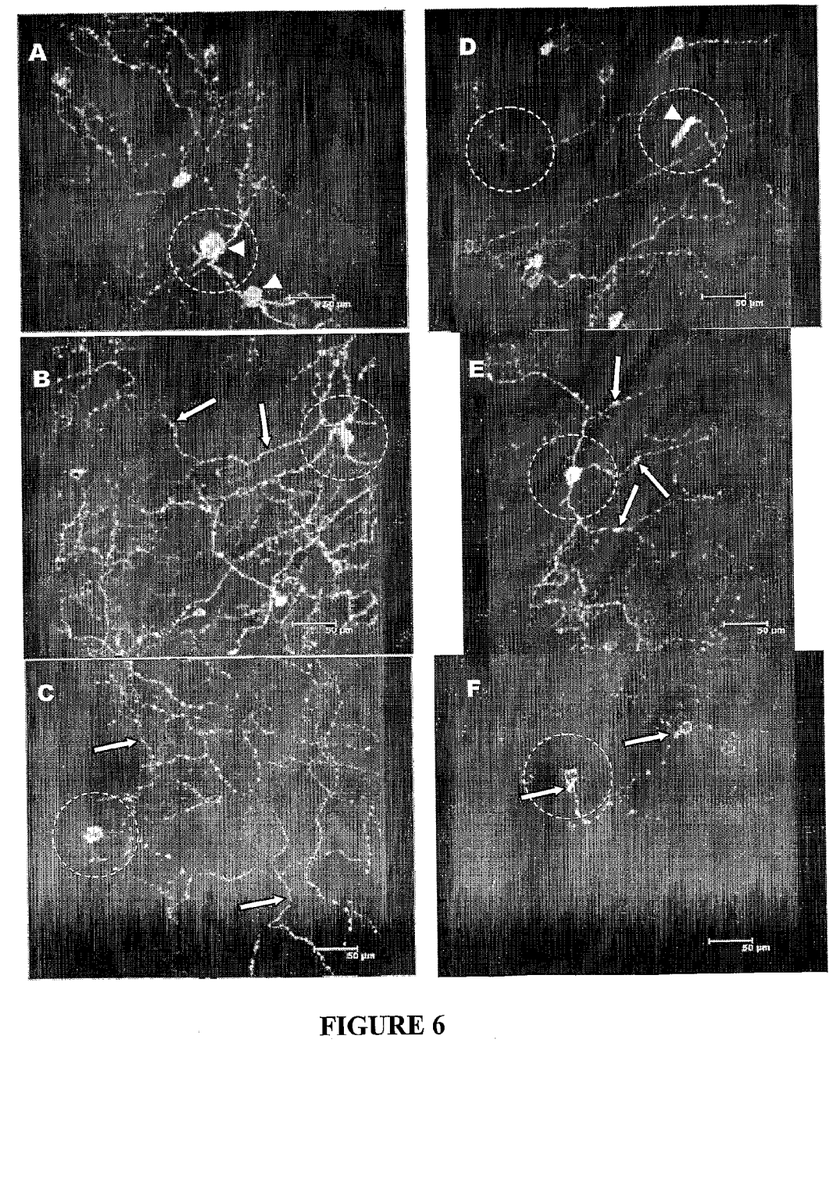
FIG. 6 shows micrograph images of morphologic abnormalities observed in mRGCs of retinas from control (A-C) and STZ-treated (D-F) mice.

FIG. 6. Morphologic abnormalities in mRGCs of three different pairs of control (A-C) vs. STZ treated (D-F) mice. Flatmount mouse retinas were labeled with an antibody to melanopsin and imaged by confocal microscopy. A qualitative Sholl analysis (37) is made where a circle (dashed white line) of 50 μm radius is centered around some of the somas and the number of dendrites intersecting with the circle gives an indication of the extent of dendritic arborisation. There are fewer dendrites radiating from the soma in the STZ set compared to the control set. Some swelling is observed in the varicosities (see thin white arrows) along the dendrites of the STZ set whereas the control set appeared normal. Morphological difference is observed in the soma (see white arrow head) of the first pair (A, D) where the soma of the STZ mice appears elongated whereas that of the control mice is more spherical in shape.

Results

Blood glucose and body weight levels. FIG. 2A shows the mean body weight of the STZ-treated mice falling gradually from day 0 to day 28 relative to the saline group where the difference between the two groups becomes significant ($p<0.05$) from day 7 onwards. FIG. 2B shows a sharp rise in the mean blood glucose level of the STZ treated mice, relative to the saline, where the difference in mean blood glucose levels becomes significant ($p<0.01$) from day 7 onwards. The STZ treated mice exhibit symptoms of polydipsia and polyuria from day 7 onwards.

In vivo imaging of retinal AF in diabetic mice. FIG. 3 shows a representative pair of selected time-lapse AF retinal images acquired from the RGC layer over 275 s from day 28 saline and STZ treated C57BL/6J mice. Both pupils exhibit PLR characterized by an initial decrease in AF (pupillary constriction) followed by a gradual increase in AF (light adaptation). But the STZ case shows a faster initial constriction and slower light adaptation when compared to the saline case. This trend is also reflected in the corresponding AF intensity profile of both pupils in FIGS. 3C and D with respect to the corresponding base-line profiles in FIGS. 3A and B. The AUC is computed from the shaded regions under the curve.

Data quantification and statistical analysis. The AUC was quantified for each eye of every mouse belonging to the saline (n=5) and STZ treated (n=4) groups and the data is presented in FIG. 5. The $\overline{AUC}$ value of the STZ treated group drops steadily from days 0-28. The saline group shows a higher $\overline{AUC}$ from days 7-28 relative to its base-line value. The difference between the two groups is significant on days 21 ($p<0.05$) and 28 ($p<0.05$).

Melanopsin Immunoreactivity. FIG. 6 shows a number of morphological differences between three control (FIG. 6A-C) and three STZ treated (FIG. 6D-F) mice with regards to the axons and somas of mRGCs. Firstly, the STZ treated group shows far fewer number of primary dendrites around the soma than the control group, indicative of severe atrophy. Secondly, swelling is observed in the varicosities along the dendrites of this group (see thin white arrows). Lastly, morphological differences are also observed in the somas, where the somas of the STZ group appear elongated in the first pair (A and D) or condensed in the third pair (C and F), both reminiscent of apoptotic cells, when compared to the more spherical somas in the control group.

The data from FIG. 6 suggests that the rapid constriction in the STZ treated group followed by the delayed pupillary dilation may be due to morphological and functional changes undergone in the mRGCs, although the exact mechanism is still unknown. Similar changes in the morphology of melanopsin expressing cells were also reported by Gastinger et al. in the Ins2$^{Akita/+}$ diabetic mouse model, where a link between these cells and the secondary effects of diabetes in the eye, i.e., diabetic retinopathy, was shown. The present data show that these effects can be observed within four weeks of diabetes. In fact, Martin et al. have reported that retinal neurons in the GCL of STZ treated mice undergo apoptosis as early as two weeks after the onset of diabetes. Therefore, PLR under the excitation of high intensity blue light can be an effective in vivo physiological marker for studying the early effects of diabetic retinopathy.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

As used in this specification and the appended claims, the singular forms "a", "an" and "the" include plural reference unless the context clearly dictates otherwise. As used in this specification and the appended claims, the terms "comprise", "comprising", "comprises" and other forms of these terms are intended in the non-limiting inclusive sense, that is, to include particular recited elements or components without excluding any other element or component. Unless defined otherwise all technical and scientific terms used herein have the same meaning as commonly understood to one of ordinary skill in the art to which this invention belongs.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

REFERENCES

Aiello L P, Gardner T W, King G L, Blankenship G, Cavallerano J D, Ferris F L, Klein R: Diabetic retinopathy. *Diabetes Care* 21:143-156, 1998

Saine P J: Landmarks in the historical development of fluorescein angiography. *Journal of Ophthalmic Photography* 15:17-23, 1993

Antonetti D A, Barber A J, Bronson S K, Freeman W M, Gardner T W, Jefferson L S, Kester M, Kimball S R, Krady J K, Lalloue K F, Norbury C C, Quinn P G, Sandirasegarane L, Simpson I A, Grp JDRC: Diabetic retinopathy—Seeing beyond glucose-induced microvascular disease. *Diabetes* 55:2401-2411, 2006

Schwartz S G, Flynn H W: Pharmacotherapies for Diabetic Retinopathy: Present and Future. *Experimental Diabetes Research*, 2007

Lieth E, Gardner T W, Barber A J, Antonetti D A, Penn State Retina Res G: Retinal neurodegeneration: early pathology in diabetes. *Clinical and Experimental Ophthalmology* 28:3-8, 2000

Lorenzi M, Gerhardinger C: Early cellular and molecular changes induced by diabetes in the retina. *Diabetologia* 44:791-804, 2001

Gardner T W, Antonetti D A, Barber A J, Lalloue K F, Levison S W, Penn State Retina Res G: Diabetic retinopathy: More than meets the eye. *Survey of Ophthalmology* 47:S253-S262, 2002

Smith S B: The impact of diabetes on neuronal, glial, and vascular cells of the retina. In *Retinal Degenerations*, Humana Press, 2007, p. 165-183

Serrarbassa P D, Dias A F, Vieira M F: New concepts on diabetic retinopathy: neural versus vascular damage. *Arq Bras Oftalmol* 71:459-463, 2008

Lucas R J, Douglas R H, Foster R G: Characterization of an ocular photopigment capable of driving pupillary constriction in mice. *Nature Neuroscience* 4:621-626, 2001

Hattar 5, Liao H W, Takao M, Berson D M, Yau K W: Melanopsin-containing retinal. ganglion cells: Architecture, projections, and intrinsic photosensitivity. *Science* 295:1065-1070, 2002

Tu D C, Zhang D Y, Demas J, Slutsky E B, Provencio I, Holy T E, Van Gelder R N: Physiologic diversity and development of intrinsically photosensitive retinal ganglion cells. *Neuron* 48:987-999, 2005

Wong K Y, Dunn F A, Berson D M: Photoreceptor adaptation in intrinsically photosensitive retinal ganglion cells. *Neuron* 48:1001-1010, 2005

Schmidt T M, Kofuji P: Functional and Morphological Differences among Intrinsically Photosensitive Retinal Ganglion Cells. *Journal of Neuroscience* 29:476-482, 2009

Belenky M A, Smeraski C A, Provencio I, Sollars P J, Pickard G E: Melanopsin retinal ganglion cells receive bipolar and amacrine cell synapses. *Journal of Comparative Neurology* 460:380-393, 2003

Hattar S, Lucas R J, Mrosovsky N, Thompson S, Douglas R H, Hankins M W, Lem J, Biel M, Hofmann F, Foster R G, Yau K W: Melanopsin and rod-cone photoreceptive systems account for all major accessory visual functions in mice. *Nature* 424:76-81, 2003

Lucas R J, Hattar S, Takao M, Berson D M, Foster R G, Yau K W: Diminished pupillary light reflex at high irradiances in melanopsin-knockout mice. *Science* 299:245-247, 2003

Fu Y B, Zhong H N, Wang M H H, Luo D G, Liao H W, Maeda H, Hattar S, Frishman L J, Yau K W: Intrinsically photosensitive retinal ganglion cells detect light with a vitamin A-based photopigment, melanopsin. *Proceedings of the National Academy of Sciences of the United States of America* 102:10339-10344, 2005

Sekaran S, Lupi D, Jones S L, Sheely C J, Hattar S, Yau K W, Lucas R J, Foster R G, Hankins M W: Melanopsin-dependent photoreception provides earliest light detection in the mammalian retina. *Current Biology* 15:1099-1107, 2005

Barnard A R, Hattar S, Hankins M W, Lucas R J: Melanopsin regulates visual processing in the mouse retina. *Current Biology* 16:389-395, 2006

Guler A D, Ecker J L, Lall G S, Haq S, Altimus C M, Liao H W, Barnard A R, Cahill H, Badea T C, Zhao H Q, Hankins M W, Berson D M, Lucas R J, Yau K W, Hattar S: Melanopsin cells are the principal conduits for rod-cone input to non-image-forming vision. *Nature* 453:102-+, 2008

Hankins M W, Peirson S N, Foster R G: Melanopsin: an exciting photopigment. Trends in *Neurosciences* 31:27-36, 2008

Grozdanic S D, Matic M, Sakaguchi D S, Kardon R H: Evaluation of retinal status using chromatic pupil light reflex activity in healthy and diseased canine eyes. *Investigative Ophthalmology & Visual Science* 48:5178-5183, 2007

Wang H Z, Lu Q J, Wang N L, Liu H, Zhang L, Zhan G L: Loss of melanopsin-containing retinal ganglion cells in a rat glaucoma model. *Chinese Medical Journal* 121:1015-1019, 2008

Gastinger M J, Kunselman A R, Conboy E E, Bronson S K, Barber A J: Dendrite remodeling and other abnormalities in the retinal ganglion cells of Ins2(Akita) diabetic mice. *Investigative Ophthalmology & Visual Science* 49:2635-2642, 2008

Maass A, von Leithner P L, Luong V, Guo L, Salt T E, Fitzke F W, Cordeiro M F: Assessment of rat and mouse RGC apoptosis imaging in vivo with different scanning laser ophthalmoscopes. *Curr Eye Res* 32:851-861, 2007

Leung C K, Lindsey J D, Crowston J G, Ju W K, Liu Q, Bartsch D U, Weinreb R N: In vivo imaging of murine retinal ganglion cells. *J Neurosci Methods* 168:475-478, 2008

Hreidarsson A B: Pupil size in insulin-dependent diabetes. Relationship to duration, metabolic control, and long-term manifestations. *Diabetes* 31:442-448, 1982

Devos A, Marcus J T, Reulen J P H, Peters H F M, Heimans J J, Vanderveen E A: The pupillary light reflex in diabetes-mellitus—Evaluation of a newly developed infrared light-reflection method. *Diabetes Research Clinical and Experimental* 10:191-195, 1989

Kuroda N, Taniguchi H, Baba S, Yamamoto M: Pupillary light reflex in borderline diabetes-mellitus. *Diabetes Research and Clinical Practice* 6:89-94, 1989

Fountas K N, Kapsalaki E Z, Machinis T G, Boev A N, Robinson J S, Troup E C: Clinical implications of quantitative infrared pupillometry in neurosurgical patients. *Neurocritical Care* 5:55-60, 2006

Lin B, Koizumi A, Tanaka N, Panda S, Masland R H: Restoration of visual function in retinal degeneration mice by ectopic expression of melanopsin. *Proceedings of the National Academy of Sciences of the United States of America* 105:16009-16014, 2008

Berson D M: Phototransduction in ganglion-cell photoreceptors. *Pflugers Archiv-European Journal of Physiology* 454: 849-855, 2007

Bos J E: Clinical quantitative pupillometry—The latency of pupillary constriction as measured with the iris system (preliminary-results). *Neuro-Ophthalmology* 8:299-305, 1988

Do M T H, Kang S H, Xue T, Zhong H N, Liao H W, Bergles D E, Yau K W: Photon capture and signalling by melanopsin retinal ganglion cells. *Nature* 457:281-U282, 2009

Martin P M, Roon P, Van Ells T K, Ganapathy V, Smith S B: Death of retinal neurons in streptozotocin-induced diabetic mice. *Investigative Ophthalmology & Visual Science* 45:3330-3336, 2004

Sholl D A: Dendritic organization in the neurons of the visual and motor cortices of the cat. *Journal of Anatomy* 87:387-406, 1953

What is claimed is:

1. A method of monitoring retinopathy in a subject, the method comprising:
   directing high intensity blue light produced by a confocal light source at the retina of an eye of the subject;
   measuring autofluorescence of the retina in response to the blue light over a total time period to obtain an autofluorescence intensity profile; and
   processing the autofluorescence intensity profile to assess the retinopathy status of the retina.

2. The method of claim 1, wherein the blue light has a wavelength of from about 485 nm to about 490 nm.

3. The method of claim 1, wherein the blue light has a wavelength of about 488 nm.

4. The method of claim 1, wherein a laser light source is used to produce the blue light.

5. The method of claim 1, wherein the confocal light source is provided by a confocal scanning laser ophthalmoscope.

6. The method of claim 1, wherein the processing comprises integrating area under the curve for the autofluorescence intensity profile.

7. The method of claim 1, wherein assessing comprises comparing the processed autofluorescence intensity profile with a processed autofluorescence intensity profile obtained for retina of a non-diseased individual.

8. The method of claim 1, wherein assessing comprises comparing the processed autofluorescence intensity profile with a processed autofluorescence intensity profile obtained for the same retina of the subject.

9. A diagnostic tool for monitoring retinopathy, the diagnostic tool comprising:
   a confocal light source for generating high intensity blue light;
   a detector for detecting autofluorescence of a retina in response to the blue light;
   a memory, said memory storing instructions; and
   a processor in communication with said light source, said detector and said memory, said processor executing instructions to:
      activate said light source to generate said high intensity blue light directed at the retina of an eye of a subject;
      obtain an autofluorescence profile over a total time period from measurements at said detector; and
      process said autofluorescence intensity profile to assess the retinopathy status of the retina.

10. The diagnostic tool of claim 9, wherein said light source is a laser light source.

11. The diagnostic tool of claim 9, wherein said light source is a confocal scanning laser.

12. The diagnostic tool of claim 11, wherein said confocal scanning laser produces light at a wavelength of about 485 nm to about 490 nm.

13. The diagnostic tool of claim 11, wherein said confocal scanning laser produces light at a wavelength of about 488 nm.

14. A computer-readable medium storing executable instructions that, upon execution by a processor of a computing device, causes said computing device to facilitate monitoring of retinopathy by:
  generating high intensity blue light from a confocal light source for directing at the retina of an eye of a subject;
  measuring autofluorescence of the retina in response to the blue light over a total time period to obtain an autofluorescence profile; and
  processing the autofluorescence intensity profile to assess the retinopathy status of the retina.

15. The method of claim 1, wherein the confocal light source is a confocal scanning laser ophthalmoscope, the blue light has a wavelength of from about 485 nm to about 490 nm, and processing the autofluorescence intensity profile comprises integrating area under the curve for the autofluorescence intensity profile to assess the retinopathy status of the retina.

16. The diagnostic tool of claim 9, wherein the confocal light source is a confocal scanning laser ophthalmoscope, and the blue light has a wavelength of from about 485 nm to about 490 nm.

\* \* \* \* \*